United States Patent
Abe et al.

(10) Patent No.: US 6,733,528 B2
(45) Date of Patent: May 11, 2004

(54) IMPLANT FORMING METHOD

(75) Inventors: Keita Abe, Tokyo (JP); Masanori Nakasu, Tokyo (JP); Ichiro Ono, 4-2-406, Makomanai midorimachi 3-chome, Minami-ku, Sapporo-shi, Hokkaido (JP)

(73) Assignees: PENTAX Corporation, Tokyo (JP); Ichiro Ono, Sapporo (JP)

( * ) Notice: Subject to any disclaimer, the term of this patent is extended or adjusted under 35 U.S.C. 154(b) by 52 days.

(21) Appl. No.: 10/212,151

(22) Filed: Aug. 6, 2002

(65) Prior Publication Data
US 2003/0030170 A1 Feb. 13, 2003

(30) Foreign Application Priority Data
Aug. 9, 2001 (JP) .......................................... 2001-242244

(51) Int. Cl.[7] .............................. A61F 2/02; B29B 11/14
(52) U.S. Cl. ..................... 623/11.11; 264/113; 264/122; 264/123; 264/308
(58) Field of Search ................................. 264/113, 122, 264/123, 308; 623/11.11

(56) References Cited

U.S. PATENT DOCUMENTS

| | | | |
|---|---|---|---|
| 5,510,066 A | 4/1996 | Fink et al. | |
| 5,518,680 A | 5/1996 | Cima et al. | |
| 5,869,170 A | 2/1999 | Cima et al. | |
| 6,036,777 A | 3/2000 | Sachs | |
| 6,176,874 B1 | 1/2001 | Vacanti et al. | |
| 6,177,034 B1 | 1/2001 | Ferrone | |
| 6,338,810 B1 * | 1/2002 | Carpena et al. | ............... 264/16 |
| 6,402,517 B1 * | 6/2002 | Hozumi et al. | .......... 433/201.1 |
| 6,454,811 B1 | 9/2002 | Sherwood et al. | |

FOREIGN PATENT DOCUMENTS

| | | |
|---|---|---|
| JP | 5-192362 | 8/1993 |
| JP | 7-277790 | 10/1995 |
| WO | 00/71178 | 11/2000 |

OTHER PUBLICATIONS

English Language Abstract WO 00/71178.
"A Comparison of the Shapes of Hydroxyapatite Implants Before and After Implantation", Abe et al., published on Apr. 3, 2002 in Wiley InterScience <www.interscience.wiley.com>.

* cited by examiner

Primary Examiner—Stephen J. Lechert, Jr.
(74) Attorney, Agent, or Firm—Greenblum & Bernstein, P.L.C.

(57) ABSTRACT

A method for forming an implant having a desired shape includes the steps of (a) forming a layer of ingredient powder having a predetermined thickness composed of an ingredient powder, and (b) applying an reactant liquid to the layer in accordance with the desired shape of the implant, portions of the ingredient powder reacting with the reactant liquid being hardened. The above steps are repeated to stack a plurality of the layers having hardened portions, respectively, to form a three-dimensional implant formed by a stack of the hardened portions of the layers of the ingredient powder. The ingredient powder is a powder including at least one of a-tricalcium phosphate and tetracalcium phosphate, and a Ca/P ratio of the powder is within a range of 1.40 through 2.0.

12 Claims, 6 Drawing Sheets

IMPLANT FORMING METHOD

BACKGROUND OF THE INVENTION

The present invention relates to a method for forming a three-dimensional implant.

Conventionally, when a body of bone, for example bones of skull, cheek bone, jaw bone or the like is partially lost, implants made of artificial material are filled in the defected part, and fixed thereat.

In conventional art, the implants are typically formed as follows.

Firstly, using a two-dimensional CT, an image of a remainder of a body of bone having a defected portion is captured. Then, based on the thus captured image, a model corresponding to the remainder is formed. Next, using paper-mache pulp or the like, a model of the defected portion is made. Then, using the model of the defected portion thus formed, a female mold made of resin is formed. Then, using the female mold, a male mold is created.

Then, the male mold and a block of hydroxyapatite (HAp) are set in a copying machine, an implant as desired is formed.

When implants are formed in accordance with the forming method described above, if an implant includes a void having a complicated shape, it is sometimes difficult or substantially impossible to form an implant having a desired shaped.

Further, according to the conventional method, a relatively long time period is required for forming an implant, and it may be difficult to supply an implant for an emergency surgery.

SUMMARY OF THE INVENTION

The present invention provides an advantage in that an improved method for manufacturing an implant having a complicated shape relatively easily with a high degree of accuracy.

According to the invention, there is provided a method for forming an implant having a desired shape, which includes (a) forming a layer of ingredient powder having a predetermined thickness composed of an ingredient powder, and (b) applying an reactant liquid to the layer in accordance with the desired shape of the implant, portions of the ingredient powder reacting with the reactant liquid being hardened. It should be noted that the steps of forming and the applying are repeated to stack a plurality of the layers having hardened portions, respectively, to form a three-dimensional implant formed by a stack of the hardened portions of the layers of the ingredient powder. The ingredient powder is a powder including at least one of a-tricalcium phosphate and tetracalcium phosphate, and a Ca/P ratio of the powder is within a range of 1.40 through 2.0.

In accordance with the above method, an implant having a complicated shape can be formed relatively easily within a very limited period in time with a high dimension of accuracy.

Optionally, the ingredient powder may be a powder containing a-tricalcium phosphate, tetracalcium phosphate and calcium hydrogen phosphate, and the Ca/P ratio of the ingredient powder is within a range of 1.40 through 1.80.

According to the embodiment, the step of hardening does not add a binder.

Optionally, the method includes a step of removing the unhardened ingredient powder after the steps of forming and the hardening have been finished.

Further optionally, the reactant liquid is at least mainly composed of water, or pure water.

Still optionally, the ingredient powder may produce apatite when reacts with the reaction liquid.

Further, the mean particle size of the ingredient powder may be within a range of 5 $\mu$m through 40 $\mu$m.

Optionally, the mean thickness of the layer of the ingredient powder may be within a range of 0.1 mm through 0.5 mm.

Furthermore, the reaction liquid may be blown to the layer of ingredient powder in a form of drops.

Preferably, the porosity of the implant, which is formed in accordance with the above method, is within a range of 10 through 90 vol %.

According to another aspect of the invention, there is provided a method for forming an implant having a desired shape, which includes (a) forming a layer of ingredient powder having a predetermined thickness composed of an ingredient powder, and (b) applying an reactant liquid to the layer in accordance with a cross-sectional shape of the implant corresponding to a currently processed layer, portions of the ingredient powder reacting with the reactant liquid being hardened. The steps of forming and the applying are repeated with shifting a level of the layer so as to stack a plurality of the layers having hardened portions are formed one by one to form an implant formed by a stack of the hardened portions of the layers of the ingredient powder. The ingredient powder is a powder including at least one of a-tricalcium phosphate and tetracalcium phosphate, and a Ca/P ratio of the powder is within a range of 1.40 through 2.0.

BRIEF DESCRIPTION OF THE ACCOMPANYING DRAWINGS

FIG. 1 schematically shows a cross-sectional side view of an implant forming apparatus for forming an implant in accordance with a method according to an embodiment of the invention;

DETAILED DESCRIPTION OF THE EMBODIMENTS

Hereinafter, a method of forming a three-dimensional implant according to an embodiment of the present invention will be described with reference to the accompanying drawings.

Figure 6:
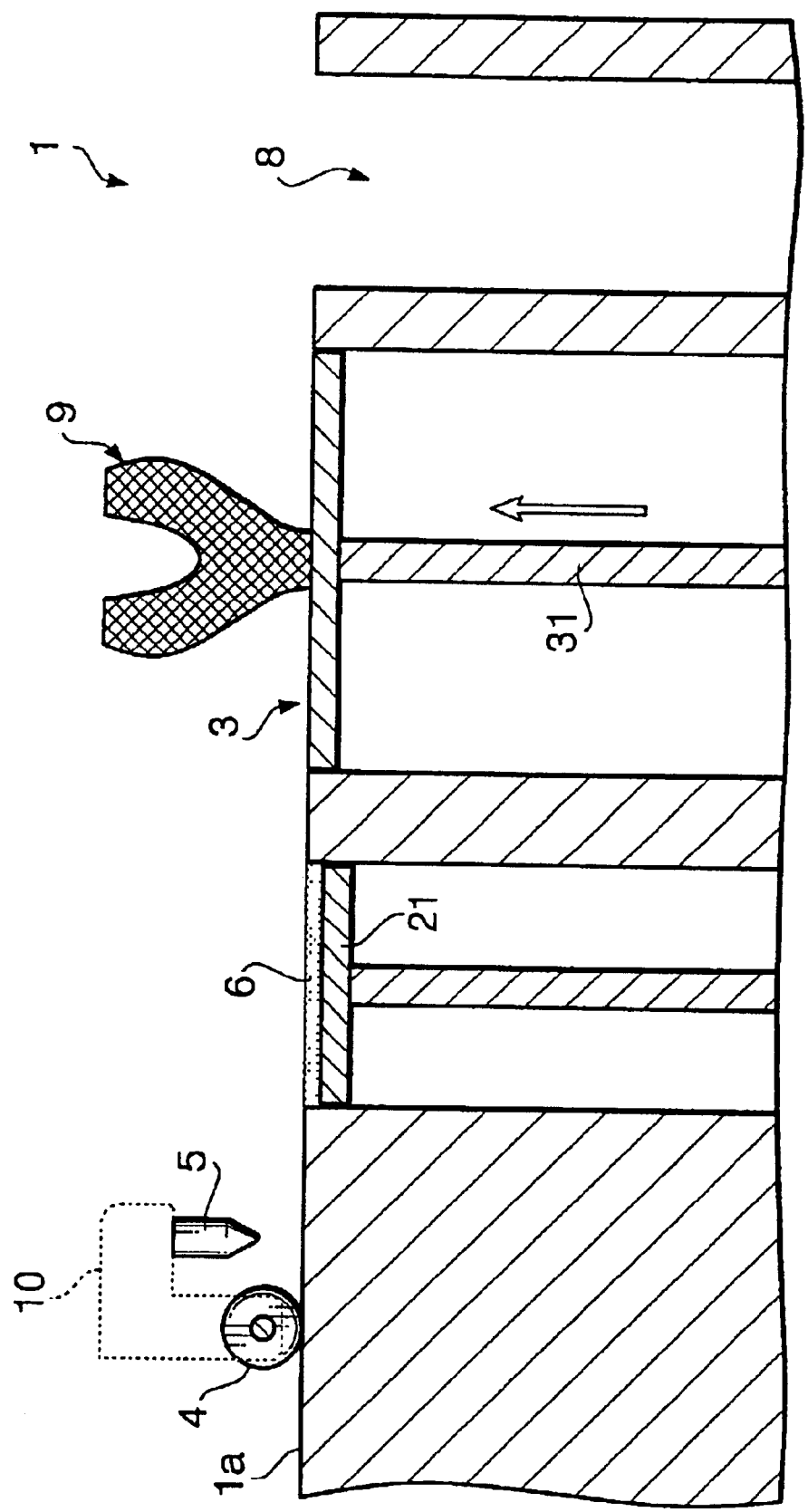
FIG. 6 shows the implant obtained in accordance with the forming method according to the embodiment of the invention.

FIGS. 1 through 4 schematically show cross-sectional views of an implant forming apparatus 1 at various stages of an implant forming method in accordance with an embodiment of the invention. FIG. 6 shows an example of an implant formed in accordance with the method.

Figure 1:
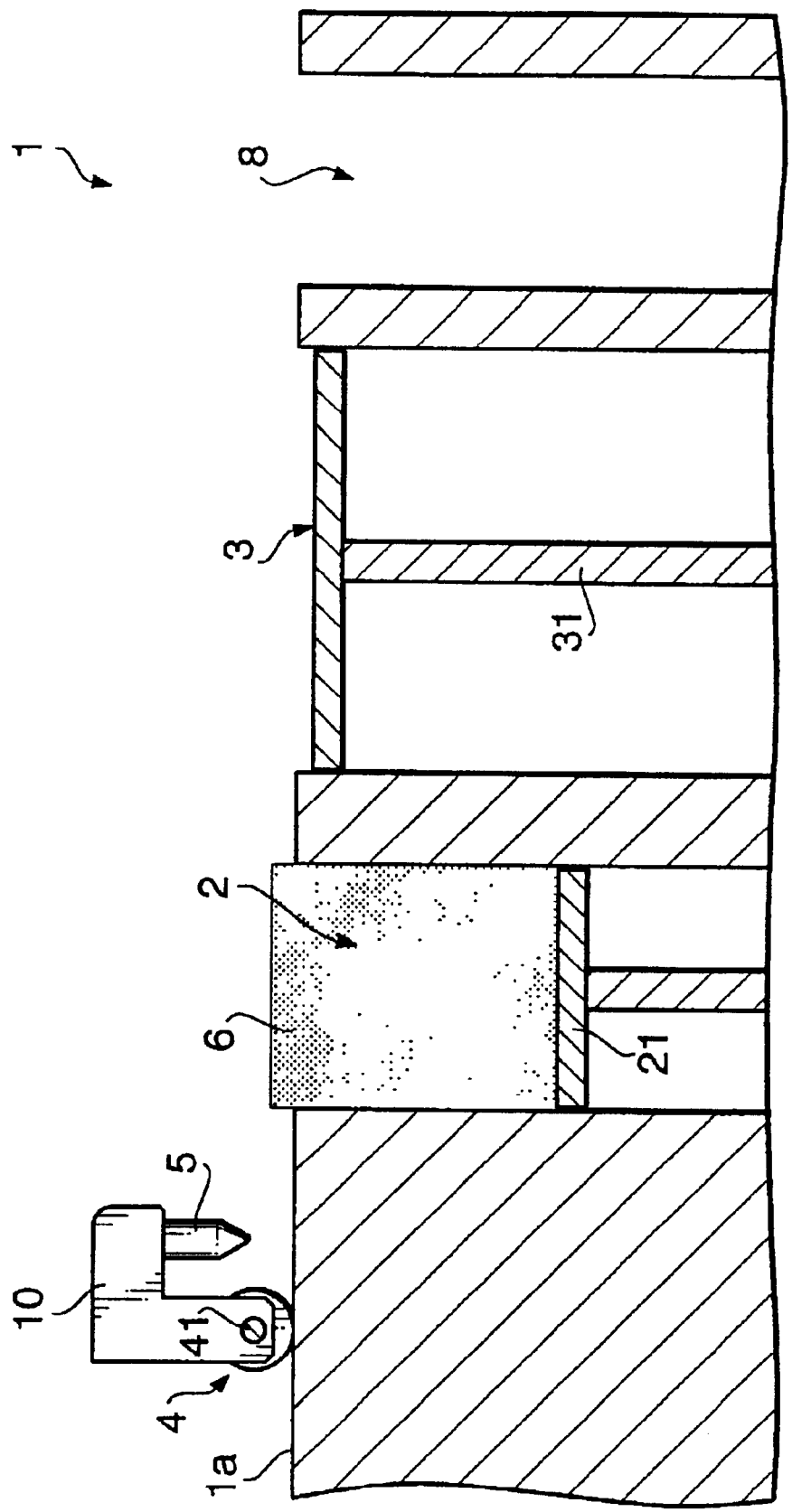

As shown in FIG. 1, the implant forming apparatus 1 has an ingredient supplying tank 2, an implant forming stage 3, a roller 4 and a supplying head 5. It should be noted that the implant forming apparatus 1 has a certain width in a direction perpendicular to a plane of the drawing.

In the ingredient tank 2, powdered ingredient 6 used for forming an implant 9 is stored. A bottom 21 of the ingredient tank 2 has a piston structure, which is movable in a vertical direction (i.e., in an up-down direction in FIG. 1). Since various mechanisms have been conventionally known for realizing such a movement, and any of such mechanisms can apply to the implant forming apparatus 1, the piston mechanism will not be described in detail.

The ingredient is carried from the ingredient tank 2 to the implant forming stage 3, on which the ingredient material is reacted with a reactant liquid 7 to form the implant. According to the embodiment, the ingredient powder is hardened when reacted with the reactant liquid, which will be described in detail later. The implant forming stage 3 is also provided with a piston mechanism 31, and movable in the vertical direction (i.e., in the up-down direction in FIG. 1).

The roller 4 is supported by a supporting device 10 so as to be rotatable about a shaft 41 that is held in the supporting device 10. The supporting device 10 is movable in a horizontal direction (i.e., in right- and left-hand direction in FIG. 1). As the supporting device 10 moves in the horizontal direction, the roller rotates and moves on the ingredient supplying tank 2 and the implant forming stage 3. As will be described in detail below, as the roller 4 moves, some of the powered ingredient 6 is carried onto the implant forming stage 3 to form a layer 61 of the ingredient on the implant forming stage 3.

The liquid supplying head 5 is held by the supporting device 10, and is configured to blow out the reactant liquid 7 toward at least a part of the ingredient layer 61 on the implant forming stage 3. The liquid supplying head 5 is movable, with respect to the supporting device 10, in a direction perpendicular to the plane of FIG. 1. As the supporting device 10 moves in the horizontal direction, while the liquid supplying head 5 moves in a direction perpendicular to the plane of FIG. 1, the liquid supplying head 5 scans a two-dimensional area, which corresponds to the layer 61 of the ingredient powder 6. The reactant liquid 7 is blown out of the liquid supplying head 5 in accordance with a pattern which is a cross-sectional shape of a desired implant taken along plane perpendicular to the plane of FIG. 1 and parallel with the horizontal direction (i.e., right-and-left direction in FIG. 1).

A method for forming the implant using the above-described implant forming apparatus 1 will be described in detail with reference to FIGS. 2 through 4.

The method includes the steps of:

(a) forming a layer 61 of ingredient powder 6 on the implant forming stage 3;

(b) blowing out the reactant liquid 7 to at least a part of the layer 61 of the ingredient powder 6; and (c) moving the implant forming stage 3 downward, and repeating the steps (a) and (b).

By steps (a) and (b), on a layer 61 of the ingredient powder 6, the reactant liquid 7 is applied to the ingredient powder in accordance with a cross-sectional shape of the implant to be formed. The portions of the ingredient powder 6 applied with the reactant liquid 7 are hardened, with the remaining portions unhardened. By repeating the steps (a) and (b) with moving the implant forming stage 3 downward at every execution of the steps (a) and (b), a cross-sectional shape of the implant is formed as a hardened portion of the ingredient powder layer by layer. Finally, a stack of layers 61 of hardened portions form the implant shape.

Each step will be described in detail hereinafter.

First Step

At an initial stage, the bottom plate 21 is positioned so that the ingredient powder 6 is slightly protruded with respect to a top surface 1a of the apparatus 1, as shown in FIG. 1. Then, the supporting device 10 is driven to move to pass over the ingredient material tank 2 and the implant forming stage 3 (i.e., the supporting device 10 moves from the left-hand side of the ingredient material tank 2 to the right-hand side end of the implant forming stage 3). FIG. 2 shows a status when the above movement is finished.

With this movement, the roller 4 moves, with rotating about the shaft 41, carries the protruded portion of the ingredient powder 6 in the ingredient material tank 2 onto the implant forming stage 3 to form the layer 61.

The mean thickness of the layer 61 is not limited to a specific value, but it should be determined based on characteristics of the ingredient powder 6 and the reactant liquid 7. Generally, the mean thickness may be in a range of 0.1 mm through 0.5 mm. Preferably, the mean thickness is in a range of 0.1 mm through 0.3 mm.

If the mean thickness is too small, a dispersion of the thickness of the layer 61 tends to increase. Further, if the implant 9 to be formed is relatively large in size, a time period for forming the entire implant may become long, which lowers a productivity of the implant.

If the mean thickness is too large, the reactant liquid 7 may not cause sufficient reaction, and a mechanical strength of the resultant implant may not be sufficient. Further, the accuracy in size tends to be lowered.

It should be noted that residual ingredient powder 6, which is carried from the ingredient supplying tank 2 and does not contribute to form the layer 61 is collected by an ingredient collection tank 8.

Second Step

Next, the reactant liquid 7 is applied to a part of the layer 61 formed on the implant forming stage 3 in accordance with a cross-sectional shape of the implant 9 to be formed. Then, between the powdered ingredient layer 61 and the reactant liquid 7, chemical reaction is induced, thereby the ingredient powder 6 is hardened to form a hardened section 62.

It should be noted that, according to the embodiment, the ingredient 6 is hardened by the chemical reaction between the ingredient 6 and the reactant liquid 7. That is, the ingredient powder 6 can be hardened without adding a binder. Therefore, it is possible to form an implant including less impurities. Such an implant is expected have an excellent affinity to living body.

According to the embodiment, the reactant liquid 7 is supplied from the supplying head 5 as drops of the liquid blown out therefrom. Specifically, as mentioned above, the liquid supplying head 5 reciprocally moves in a width direction (i.e., in a direction perpendicular to the plane of FIG. 3), while the roller 4 moves in the horizontal direction (i.e., a direction parallel to the right-and-left direction in FIG. 3), thereby the reactant liquid 7 being applied in accordance with a two-dimensional pattern.

Since the reactant liquid 7 is supplied as described above, the reactant liquid 7 can be supplied with a high accuracy and efficiently to designated portions of the layer 61 of the ingredient powder 6. As a result, the accuracy of the implant in size can be improved, and the productivity is also improved.

Figure 3:
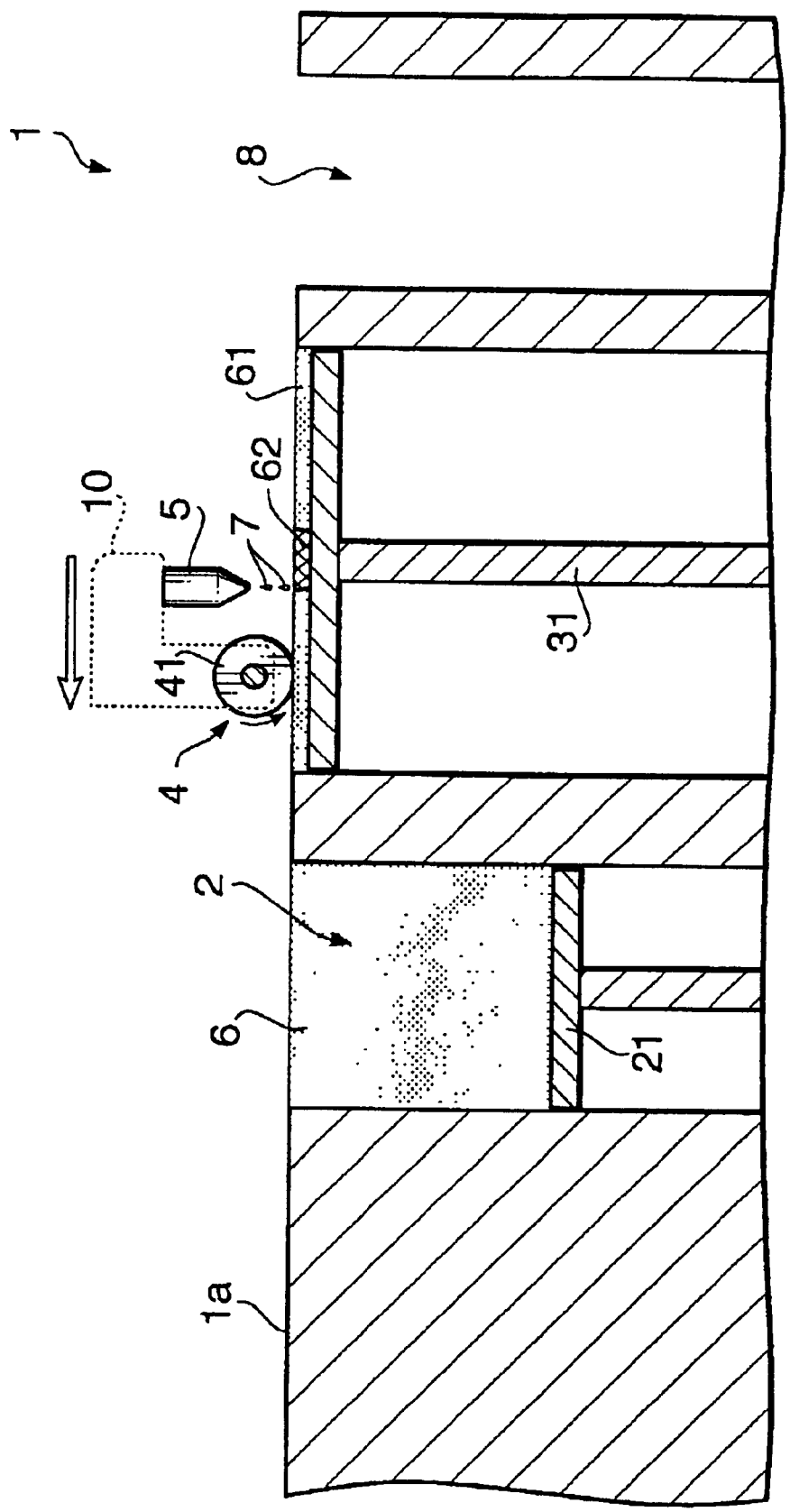
FIG. 3 shows the implant forming apparatus when a second step of the forming method is performed.

As shown in FIG. 3, in the step of supplying the reactant liquid 7, the supplying head 5 moves above the ingredient supplying tank 2 and the implant forming stage 3, along the substantially horizontal direction, and blows out the reactant liquid 7 so that portions corresponding to the cross-sectional shape of the implant 9 are formed to be the hardened section 62.

The cross-sectional shape of the implant 9 is generally determined based on the data extracted from the CT film and the like. If it is expected that the hardened section 62 shrinks during following process, the pattern is determined taking the shrinking effect into account.

It should be noted that the hardened section 62 is formed across the entire thickness of each layer 61.

Third Step

Figure 4:
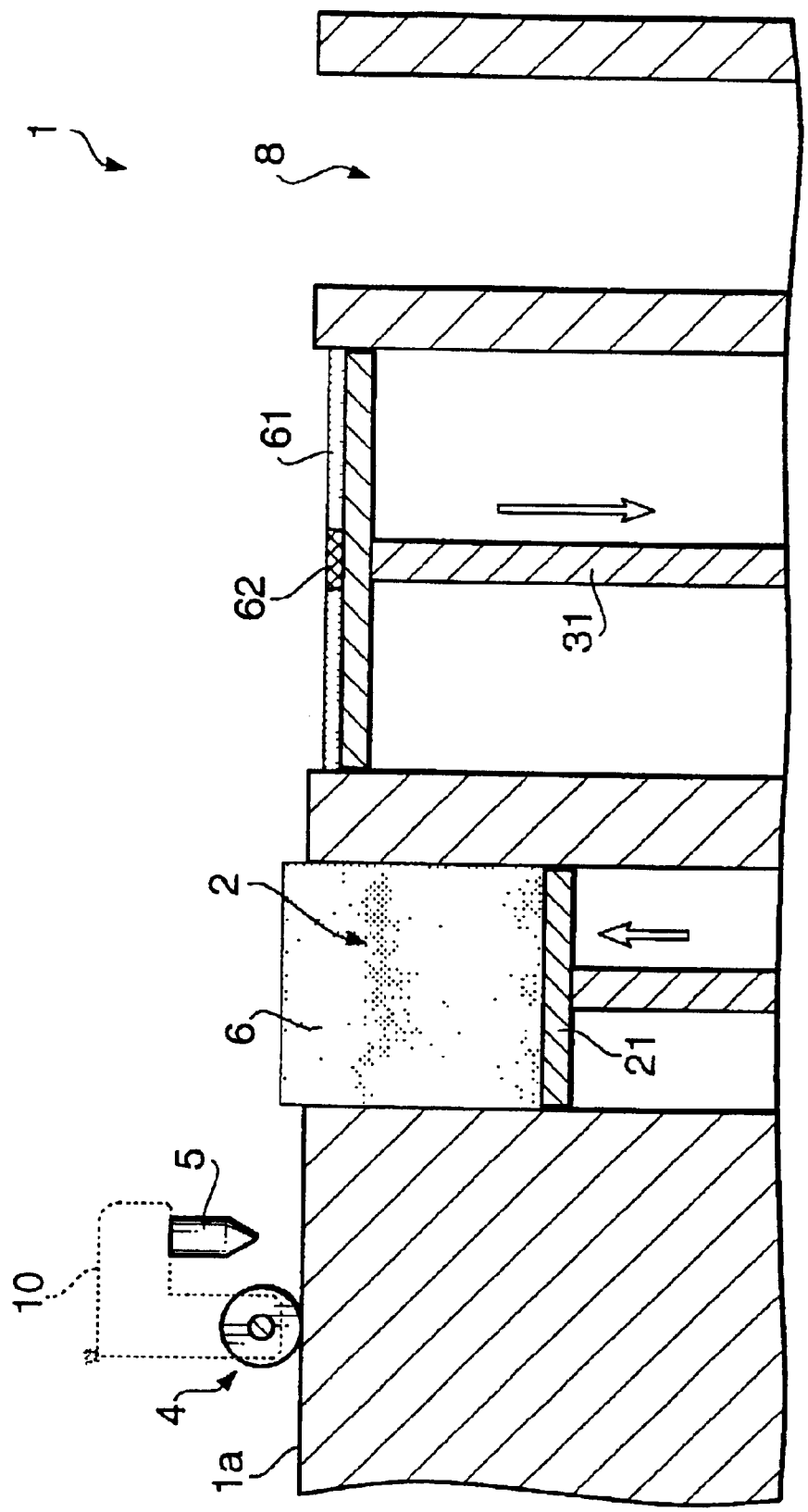
FIG. 4 shows the implant forming apparatus when a third step of the forming method is performed.

Next, as shown in FIG. 4, the bottom plate 21 of the ingredient supplying tank 2 is moved upward to adjust a level of the upper surface of the ingredient powder 6 (i.e., the protruded amount thereof). At the same time, the implant forming stage 3 is lowered to adjust a level of the upper surface of the layer 61 (i.e., the height of a layer 61 to be formed by the successively supplied ingredient powder 6). The moving amount of the bottom plate 21 preferably corresponds to an amount of the ingredient powder 6 supplied from the ingredient supplying tank 2 to the implant forming stage 3 at the first step. Further, the moving amount of the implant forming stage 3 is preferably the same as the mean thickness of the layer 61 formed in the first step. With the above configuration, the thickness of each layer 61 successively formed will be maintained substantially constant.

Figure 5:
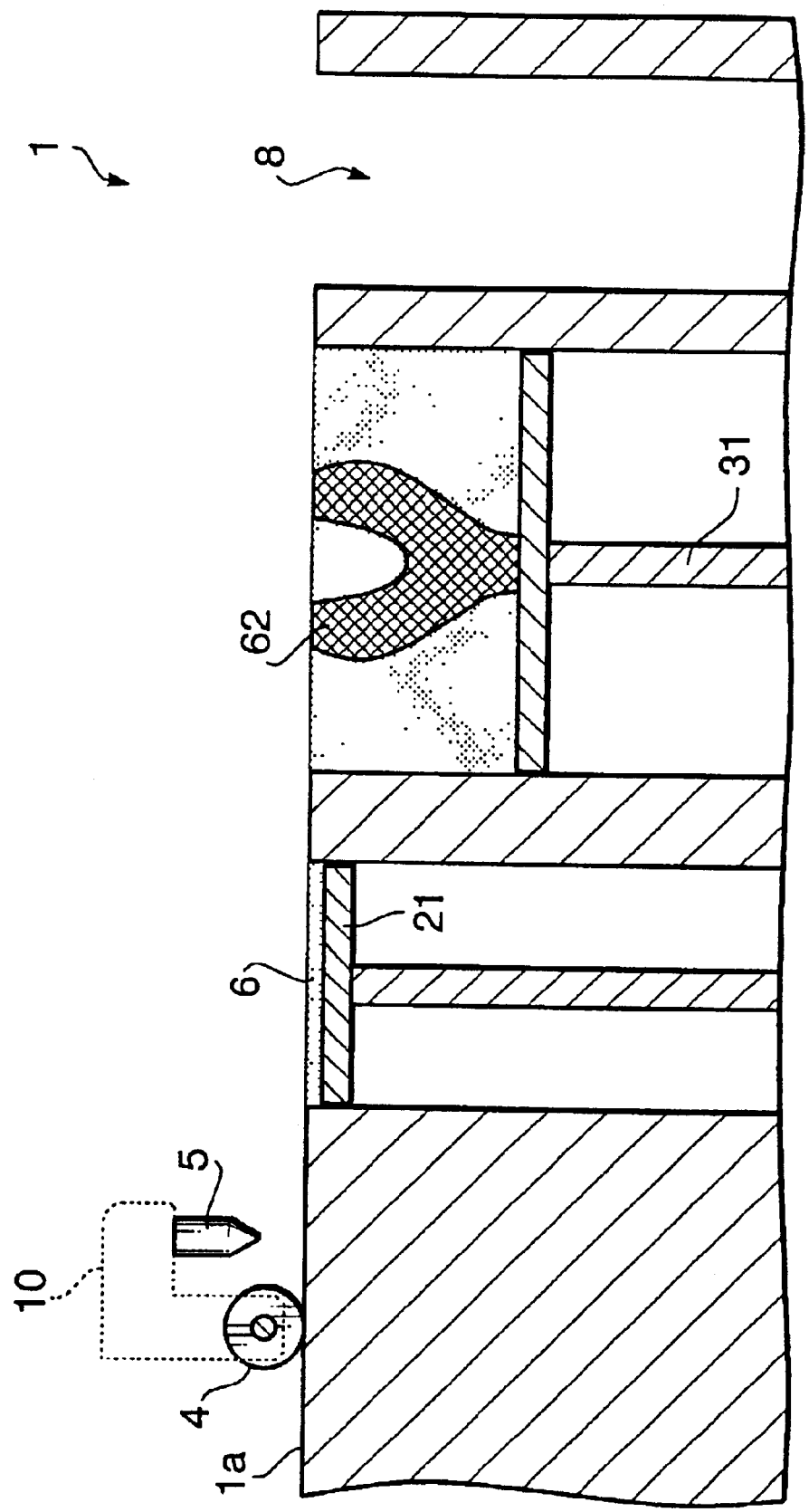
FIG. 5 shows the implant forming apparatus after the first through third steps of the forming method have been performed.

Repeating the first through third steps, a plurality of layers 61 are stacked and the hardened section 62 forms a desired implant shape as shown in FIG. 5. It should be noted that the hardened sections 62 of the subsequent layers 61 are connected at portions facing each other. Therefore, as the processes proceed, the hardened sections 62 form a three-dimensional substance.

As described above, by stacking the hardened section 62 of each layer 61, the implant 9 is formed. According to this method, even if the implant 9 has a relatively complicated shape, it can easily be formed. Further, the obtained implant 9 has an excellent dimensional accuracy. Furthermore, according to this method, a desired implant 9 can be formed within a relatively short period of time. Therefore, the implant 9 can be prepared even for an emergency operation.

After the implant forming method is completed, the implant forming stage 3 is lifted and unhardened ingredient powder 6 is removed, thereby the implant 9 having the desired shape is obtained. The unhardened ingredient power 6 can be removed easily, for example, by blowing air.

The implant 9 thus obtained may be subject to further treatment (e.g., sintering or impregnation with water) if necessary.

It is preferable that the implant 9 thus obtained has an appropriate porosity so that, when the implant 9 is implanted in a living body, osteoblast easily invades in the pores of the implant 9, and bone formation smoothly proceeds. As a result, the period until a stable effect of the implant 9 is obtained can be shortened. The porosity of the implant 9 is, for example, preferably 10 through 90 vol %, and more preferably 30 through 90 vol %.

If the porosity of the implant 9 is too small, the osteoblast may not invade in the pores of the implant 9 sufficiently, and bone formation does not proceed well.

If the porosity of the implant 9 is too large, a sufficient mechanical strength of the implant 9 may not be obtained.

The size of the pores (pore diameter) formed in the implant 9 is preferably 100 $\mu$m through 1000 $\mu$m. If the pore diameter is less than 100 $\mu$m, the osteoblast does not invade in the pores of the implant 9 sufficiently, and bone formation may not proceed well. If the pore diameter exceeds 1000 $\mu$m, sufficient mechanical strength of the implant 9 may not be obtained.

As described above, the ingredient powder 6 is hardened by chemical reaction between the ingredient powder 6 and the reactant liquid 7. Therefore, the ingredient powder 6 can be hardened without adding a binder. Accordingly, the implant 9 includes less impurities, and thus, it has excellent biocompatibility.

Further, both the ingredient powder 6 and reactant liquid 7 may be selected to have excellent biocompatibility. In such a case, even when the ingredient powder 6 and reactant liquid 7 remain unreacted, a harmful influence on the living body is avoidable.

Hereinafter, the ingredient power 6 and the reactant liquid 7 will be described in detail.

<Ingredient Powder>

According to the embodiment, a powder which contains a-tricalcium phosphate and/or tetracalcium phosphate, and has a Ca/P ratio of 1.40 through 2.0 is used as the ingredient powder 6.

Examples of such an ingredient powder 6, is a mixture containing a-tricalcium phosphate and/or tetracalcium phosphate, and at least one of hydroxy apatite, β-tricalcium phosphate, and calcium hydrogen phosphate.

Among above examples, it is particularly preferable that the ingredient powder 6 is a powder which contains a-tricalcium phosphate, tetracalcium phosphate and calcium hydrogen phosphate, and has a Ca/P ratio of 1.40 through 1.80. When such an ingredient powder 6 is used, the implant 9 have especially excellent biocompatibility and excellent mechanical strength can be obtained.

The a-tricalcium phosphate and tetracalcium phosphate to be used may be separately produced by well-known methods, or a mixture of a-tricalcium phosphate and tetracalcium phosphate which are obtained by sintering hydroxy apatite.

When the hydroxy apatite is sintered, a sintering condition will be 1150° C. through 1450° C. for about one hour under decompression.

The calcium hydrogen phosphate may also be one manufactured by a well-known method, and either anhydride ($CaHPO_4$) orhydrate (for example, dihydrate ($CaHPO_4.2H_2O$), etc.) may be used.

The ingredient powder 6 may contain, as appropriate, fluoroapatite, octacalcium phosphate, calcium pyrophosphate and the like, in addition to the abovementioned substances.

The ingredient powder 6 according to the embodiment chemically reacts with the reactant liquid 7 and is hardened.

As mentioned above, the Ca/P ratio of the ingredient powder 6 is 1.40 through 2.0, and is preferably 1.40 through 1.80, and more preferably 1.40 through 1.70. If the Ca/P ratio is less than 1.40 or exceeds 2.0, the hardening reaction does not proceed at a sufficient reaction rate, and an obtained implant 9 may not have a sufficient mechanical strength.

In the ingredient powder 6, additives such as an X-ray contrast medium, an antibacterial agent, and a thickener or the like may be contained as necessary. As the X-ray contrast medium, there is no limitation, and various types can be used. For example, barium sulphate, basic bismuth carbonate, and iodoform or the like can be used, and one or more kinds among the above can be used. As an antibacterial agent, iodoform, chlorhexidine or the like can be used.

The mean particle size of the ingredient powder 6 is preferably 5 $\mu$m through 40 $\mu$m, and more preferably 5 $\mu$m through 20 $\mu$m.

If the mean particle size of the ingredient powder 6 is less than the abovementioned lower limit, it becomes difficult to handle the ingredient powder 6. Also, if the mean particle size of the ingredient powder 6 is less than the lower limit, the porosity of the obtained implant 6 becomes too low, and the bone formation may not proceed well.

If the mean particle size of the ingredient powder 6 exceeds the upper limit, depending on the size of the implant 9 obtained by the abovementioned forming process, sufficient dimensional accuracy may not be obtained.

[Reactant Liquid]

Any type of reactant liquid 7 can be used if it chemically reacts with the ingredient powder 6 and hardens the same. Preferably, the reactant liquid 7 is water or liquid mainly composed of water.

If such an reactant liquid 7 is used, the hardened section 62 formed by reaction between the ingredient powder 6 and the reactant liquid 7 has a superior mechanical strength. In particular, if water or a liquid mainly composed of water is used as the reactant liquid 7, apatite (hydroxy apatite or octacalcium phosphate) is produced by reaction with the ingredient powder 6. It is known that the apatite has excellent biocompatibility. Therefore, a highly secure implant 9 can be provided.

In the reactant liquid 7, as components other than water, various preparations may be contained. For example, organic acids such as acetic acid, lactic acid, citric acid, malic acid, malonic acid, succinic acid, glutaric acid, tartaric acid, polyacrylic acid, and gluconic acid or the like, sodium salts of the abovementioned organic acids, organic acid salts such as potassium salt, inorganic acids such as phosphoric acid or the like, inorganic acid salts such as sodium phosphate, sodium carbonate, potassium phosphate, and potassium carbonate or the like, pH adjusters, thickeners, X-ray contrast media, antibacterial agents, monosaccharides such as glucose and fructose or the like, disaccharides such as saccharose and maltose or the like, polysaccharides such as cellulose, chitin, and chitosan or the like, bone morphogenic proteins such as BMP or the like, and prostaglandin or the like may be included in the reactant liquid 7.

The implant forming method and the implant are described as an exemplary embodiment of the invention, however, the invention is not limited to the configuration described above.

For example, although the implant forming apparatus 1 is described such that the roller 4 and the liquid supply head 5 integrally move, however, the roller and the liquid supply head can be configured to move independently from each other.

Concrete Example

Next, a concrete example according to the embodiment of the invention will be described.

Formation of Implant

EXAMPLE 1

Based on the CT films imaging a head of a patient who had a bone deficient portion in his/her head, an implant having a shape corresponding to the bone deficient portion was formed.

The implant was formed according to the method described above with reference to FIGS. 2 through 4.

As the ingredient powder 6, a powder (Ca/P ratio: 1.44; and the average particle size: 10 $\mu$m) containing a-tricalcium phosphate, tetracalcium phosphate, and calcium hydrogen phosphate-2-hydrate at a mole ratio of 2:1:3 was used. As an reactant liquid, pure water was used.

The mean thickness of the respective layers formed at the implant forming stage in the first process was 0.1 mm.

Figure 2:
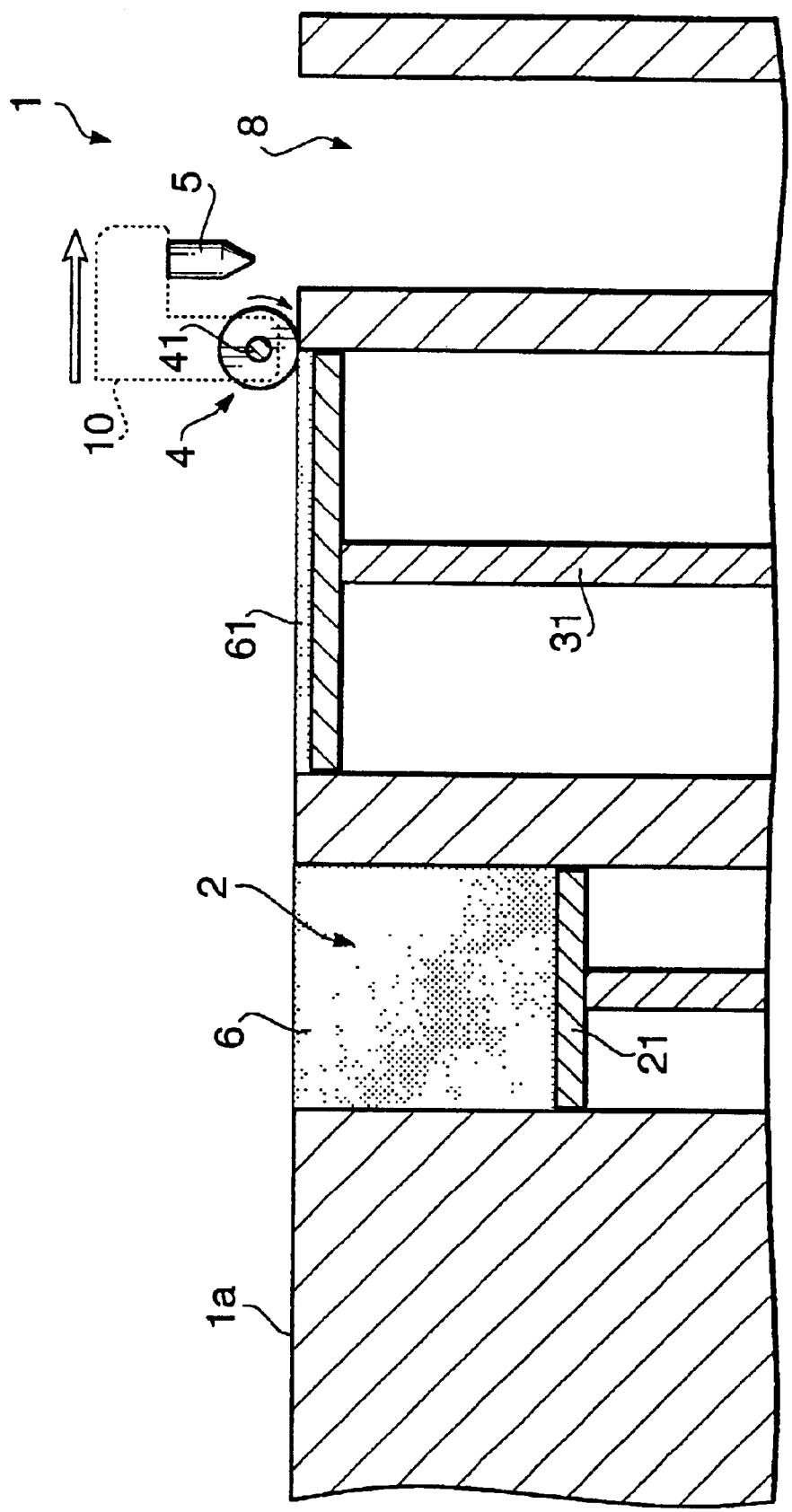
FIG. 2 shows the implant forming apparatus when a first step of the forming method is performed.

The processes shown in FIGS. 2 through 4 were repeated by a plurality of times, and the desired implant shape was formed by the hardened section 62. Thereafter, unhardened ingredient powder 6 was removed by blowing air to obtain the desired implant 9. The porosity of the implant 9 thus obtained was 40 vol %.

Comparative Example 1

Based on the CT films imaging the head of a patient who had a bone deficient portion in his/her head, a model having a shape corresponding to the remaining section of the bone including the bone deficient portion was manufactured using wood.

Next, paper-mache pulp was filled into the bone deficient portion of this model, and a model corresponding to the bone deficient portion was shaped.

The bone deficient portion formed from the paper-mache pulp was modeled with a resin material, whereby a female mold was prepared, and a male mold was prepared using the female mold.

Thereafter, this male mold and a block of hydroxy apatite are set into a copy shaping machine to process the block, whereby a formed body was obtained.

The formed body was sintered in an electric furnace at 1200° C. for 4 hours, whereby an implant having the desired shape was manufactured.

The formed body was formed so as to have dimensions in which thermal contraction when sintered were taken into consideration.

Comparative Example 2

An implant was formed in the same manner as in the EXAMPLE 1 except that hydroxy apatite (mean particle size: 10 $\mu$m) was used as the ingredient powder and cyanoacrylate (binder) was used in place of the reactant liquid.

Evaluation

In the EXAMPLE 1, the implant could be formed in a relatively short time.

The obtained implant reproduced the complicated shape in fine details including gaps, and had excellent dimensional accuracy.

When the components of the implant were analyzed, no biotoxic impurities were detected. Therefore, it is considered that the obtained implant has excellent biocompatibility, and hardly presents any harmful influences to a living body.

On the other hand, in Comparative Example 1, it took an extremely long time to form the implant.

Further, the obtained implant was poor in reproducibility at a portion having a complicated shape, and also poor in dimensional accuracy.

The implant obtained in Comparative Example 2 was relatively good in dimensional accuracy, however, when the components thereof were analyzed, cyanoacrylate was detected. Therefore, it is considered there is a possibility that the thus obtained implant has poor biocompatibility and may present harmful influences to a living body.

As described above, according to the embodiment of the present invention, an implant having a complicated shape can easily be formed. Further, the implant, which is excellent in dimensional accuracy, can easily be obtained.

Moreover, since the implant is formed in a relatively short time, the implant can be used for an emergency operation.

Furthermore, since the implant has excellent biocompatibility, it does not have harmful influence on a living body.

Such effects become more remarkable by properly selecting the conditions of the ingredient powder (for example, composition, average particle size, and the like) and the conditions of the reactant liquid (for example, composition, average particle size of drops).

The present disclosure relates to the subject matter contained in Japanese Patent Application No. 2001-242244, filed on Aug. 9, 2001, which is expressly incorporated herein by reference in its entirety.

What is claimed is:

1. A method for forming an implant having a desired shape, comprising:

(a) forming a layer of ingredient powder having a predetermined thickness composed of an ingredient powder; and (b) applying a reactant liquid to the layer in accordance with the desired shape of the implant, portions of the ingredient powder reacting with the reactant liquid being hardened, wherein the forming and the applying are repeated to stack a plurality of the layers having hardened portions, respectively, to form an implant formed by a stack of the hardened portions of the layers of the ingredient powder, wherein the ingredient powder is a powder including at least one of a-tricalcium phosphate and tetracalcium phosphate, and wherein a Ca/P ratio of the powder is within a range of 1.40 through 2.0.

2. The method according to claim 1, wherein the ingredient powder is a powder containing a-tricalcium phosphate, tetracalcium phosphate and calcium hydrogen phosphate, and wherein the Ca/P ratio of the ingredient powder is within a range of 1.40 through 1.80.

3. The method according to claim 1, wherein the hardening does not add a binder.

4. The method according to claim 1, further comprising removing the unhardened ingredient powder after the forming and the hardening have been finished.

5. The method according to claim 1, wherein the reactant liquid is at least mainly composed of water.

6. The method according to claim 1, wherein the ingredient powder generates apatite when the ingredient powder reacts with said reaction liquid.

7. The method according to claim 1, wherein the mean particle size of said ingredient powder is within a range of 5 μm through 40 μm.

8. The method according to claim 1, wherein the mean thickness of the layer of the ingredient powder is within a range of 0.1 mm through 0.5 mm.

9. The method according to claim 1, wherein the reaction liquid is blown to the layer of ingredient powder in a form of drops.

10. The method according to claim 1, wherein porosity of the implant which is formed in accordance with the method is within a range of 10 through 90 vol %.

11. An implant formed in accordance with an implant forming method that includes:

(a) forming a layer of ingredient powder having a predetermined thickness composed of an ingredient powder; and (b) applying a reactant liquid to the layer in accordance with the desired shape of the implant, portions of the ingredient powder reacting with the reactant liquid being hardened, wherein the forming and the applying are repeated to stack a plurality of the layers having hardened portions, respectively, to form an implant formed by a stack of the hardened portions of the layers of the ingredient powder, wherein the ingredient powder is a powder including at least one of a-tricalcium phosphate and tetracalcium phosphate, and wherein a Ca/P ratio of the powder is within a range of 1.40 through 2.0.

12. A method for forming an implant having a desired shape, comprising the steps of:

(a) forming a layer of ingredient powder having a predetermined thickness composed of an ingredient powder; and (b) applying an reactant liquid to the layer in accordance with a cross-sectional shape of the implant corresponding to a currently processed layer, portions of the ingredient powder reacting with the reactant liquid being hardened, wherein the forming and the applying are repeated with shifting a level of the layer so as to stack a plurality of the layers having hardened portions are formed one by one to form an implant formed by a stack of the hardened portions of the layers of the ingredient powder, wherein the ingredient powder is a powder including at least one of a-tricalcium phosphate and tetracalcium phosphate, and wherein a Ca/P ratio of the powder is within a range of 1.40 through 2.0.

* * * * *